(12) United States Patent
Hall et al.

(10) Patent No.: US 10,182,789 B2
(45) Date of Patent: Jan. 22, 2019

(54) TOILET WITH STETHOSCOPE

(71) Applicants: David R. Hall, Provo, UT (US); Dan Allen, Springville, UT (US); Ben Swenson, Lehi, UT (US)

(72) Inventors: David R. Hall, Provo, UT (US); Dan Allen, Springville, UT (US); Ben Swenson, Lehi, UT (US)

( * ) Notice: Subject to any disclaimer, the term of this patent is extended or adjusted under 35 U.S.C. 154(b) by 56 days.

(21) Appl. No.: 15/412,448

(22) Filed: Jan. 23, 2017

(65) Prior Publication Data
US 2017/0251996 A1    Sep. 7, 2017

Related U.S. Application Data

(60) Provisional application No. 62/303,350, filed on Mar. 3, 2016.

(51) Int. Cl.
| | |
|---|---|
| *A61L 2/10* | (2006.01) |
| *E03D 11/00* | (2006.01) |
| *A61B 7/04* | (2006.01) |
| *A61B 7/00* | (2006.01) |
| *A47K 13/24* | (2006.01) |
| *E03D 11/08* | (2006.01) |

(52) U.S. Cl.
CPC .............. *A61B 7/04* (2013.01); *A47K 13/24* (2013.01); *A61B 7/003* (2013.01); *A61L 2/10* (2013.01); *E03D 11/00* (2013.01); *E03D 11/08* (2013.01); *A61L 2202/24* (2013.01)

(58) Field of Classification Search
CPC ... A61B 7/04; A61B 7/003; A61L 2/10; A61L 2202/24; E03D 11/00; E03D 11/08; A47K 13/24
See application file for complete search history.

(56) References Cited

U.S. PATENT DOCUMENTS

| | | | | |
|---|---|---|---|---|
| 4,007,806 A | * | 2/1977 | Nobles, Jr. ............... | A61B 7/02 181/131 |
| 6,396,931 B1 | * | 5/2002 | Malilay ................... | A61B 7/04 181/131 |
| 7,823,862 B2 | * | 11/2010 | Wakil ................... | B62B 3/0643 254/2 R |
| 7,891,030 B1 | * | 2/2011 | Sutton .................... | A47K 11/06 4/483 |
| 9,756,297 B1 | * | 9/2017 | Clements ........... | G06K 9/00771 |

(Continued)

OTHER PUBLICATIONS iTouchless, White Elongated Round Touch-Free Sensor Controlled Automated toilet seat, Youtube, 2013.*
Viclean, User Guide Electronic Bidet Seat, 2014.*

*Primary Examiner* — Davetta W Goins
*Assistant Examiner* — Kuassi Ganmavo (57) ABSTRACT

We disclose a medical toilet that includes at least one stethoscope probe in the toilet lid. The stethoscope probes may be mounted on a compliant extension which extends the stethoscope probes toward a user seated on the toilet. The medical toilet may include a device which adjusts the height of the stethoscope probes to adjust for different size users and to collect measurements from different parts of a user. The medical toilet may include a device which records the sounds collected by the stethoscope and may also include a controller that proposes a diagnosis based on the sounds collected by the stethoscope. The medical toilet may also transmit recordings and other information to an external machine.

4 Claims, 7 Drawing Sheets

(56) References Cited

U.S. PATENT DOCUMENTS

| | | | | |
|---|---|---|---|---|
| 2002/0162972 | A1* | 11/2002 | Pleet | A61L 2/10 |
| | | | | 250/492.1 |
| 2003/0233034 | A1* | 12/2003 | Varri | A61B 5/1102 |
| | | | | 600/301 |
| 2007/0157376 | A1* | 7/2007 | Paz | A47C 23/002 |
| | | | | 4/540 |
| 2008/0146276 | A1* | 6/2008 | Lee | A61B 5/6887 |
| | | | | 455/556.1 |
| 2009/0056004 | A1* | 3/2009 | Soller | E03D 9/005 |
| | | | | 4/223 |
| 2009/0312638 | A1* | 12/2009 | Bartlett | A61B 5/00 |
| | | | | 600/443 |
| 2011/0034784 | A1* | 2/2011 | David | A61B 5/0205 |
| | | | | 600/301 |
| 2011/0137209 | A1* | 6/2011 | Lahiji | A61B 7/026 |
| | | | | 600/586 |
| 2014/0039330 | A1* | 2/2014 | Seo | A61B 5/0452 |
| | | | | 600/509 |
| 2015/0190110 | A1* | 7/2015 | Chong | H04R 1/46 |
| | | | | 600/528 |
| 2016/0045183 | A1* | 2/2016 | Lee | A61B 7/04 |
| | | | | 600/443 |
| 2016/0324996 | A1* | 11/2016 | Bilenko | A61L 2/10 |

* cited by examiner

TOILET WITH STETHOSCOPE

CROSS-REFERENCE TO RELATED APPLICATIONS

This application claims priority to U.S. provisional patent application Ser. No. 62/303,350 filed on Mar. 3, 2016 the entire contents of which is hereby incorporated by reference.

BACKGROUND

Field of the Invention

This disclosure relates to devices and methods for measuring physiological events to assess health status and diagnose disease.

Background of the Invention

Many people find that visiting a healthcare provider in a clinic or doctor's office takes too much time and is inconvenient. In addition, some people require medical services that are not available to them without significant travel and expense.

In some instances, optimal healthcare requires frequent measurements to collect trending data. This typically requires frequent inconvenient and costly visits to a healthcare provider. A device that collects and records physiological events which does not require a visit to a healthcare provider is needed.

A healthcare provider with often use a stethoscope to assess a user's health. Much information can be collected from a stethoscope, including assessments of the heart and lungs. A stethoscope measurement that does not require a visit to a clinic and which may be conducted conveniently and frequently is needed.

BRIEF SUMMARY OF THE INVENTION

We disclose a medical toilet that includes one or more different types of stethoscopes. The medical toilet may include a toilet lid where one or more stethoscope probes may be positioned. The user may sit on the toilet seat as one would sit on a traditional toilet. The toilet lid may include a compliant extension which may include an inflatable bladder or other device to extend the stethoscope probes toward a seated user. The stethoscope probes may be positioned on the outer surface of the compliant extension so that the stethoscope probes face a user seated on the toilet seat of the medical toilet. Upon actuation, the compliant extension may extend outward toward the user. The stethoscope probes are thus placed against the user's back so that a measurement may be taken. After the measurement is complete, the compliant extension may retract back toward the toilet lid.

The medical toilet may include a height adjustment apparatus which may raise or lower the stethoscope probes to collect measurements from different areas on a user's back or to adjust to the height of different users.

The medical toilet may include a sound recorder which may record sounds detected by the stethoscope probes. The medical toilet may also include a controller which may conduct one or more analyses of the sounds. The analyses may include a proposed diagnosis. The medical toilet may include a data port which may be used to transmit recorded sounds collected by the stethoscope probes and analyses of the sounds performed by the controller.

DETAILED DESCRIPTION OF THE INVENTION

Definitions

Toilet, as used herein, means a device that collects biological products of a mammal, including urine and feces.

Medical toilet, as used herein, means a toilet that conducts one or more measurements relevant to a user's health status.

User, as used herein, means any mammal, human or animal, from which a measurement is taken using the medical toilet disclosed herein.

Healthcare provider, as used herein, means any individual who performs a task, mental or physical, in relation to health-related services provided to a user.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a medical toilet which may function to collect and dispose of bodily waste much like a traditional toilet and may be installed in a user's home. The toilet includes a toilet seat with a front section and a rear section. The front section is that side nearest a user's front side when the user is seated as one would traditionally sit on a toilet. The rear side is that side nearest a user's back when the user is seated as one would traditionally sit on a toilet. The rear side is nearest the toilet tank as it would be positioned on a traditional toilet.

The medical toilet includes a toilet lid which may be positioned at the rear section of the toilet seat using hinges or other means known in the art to secure a toilet lid to a toilet. The toilet lid also may include a compliant extension which may extend outward and contract backward from the toilet lid. Accordingly, the compliant extension may extend toward and away from a user seated on the medical toilet.

A stethoscope probe may be positioned on the outer surface of the compliant extension. Thus, as the compliant extension moves outward away from the toilet lid, the stethoscope probe moves toward the back of a user seated on the toilet seat. When the measurement is complete, the compliant extension may retract away from the back of the user.

In some embodiments, the medical toilet includes more than one stethoscope probe. In some embodiments, the medical toilet includes two stethoscope probes. One of the two stethoscope probes may be positioned lateral to the other on the outer surface of the compliant extension. Accordingly, the two stethoscope probes may simultaneously collect measurements from the left and right side of a user's back as the user is seated on the toilet seat. Alternatively, the two stethoscope probes may collect measurements one at a time. In this embodiment, one stethoscope probe is actuated while the other is inactive.

In some embodiments, the medical toilet includes four stethoscope probes. In one embodiment, the four stethoscope probes are positioned on the four corners of a square or rectangle on the outer surface of the compliant extension. Accordingly, the four stethoscope probes may be used to simultaneously collect measurements from the upper right, upper left, lower right, and lower left of a user's back. Alternatively, the four stethoscope probes may collect measurements one at a time in a variety of combinations. In this embodiment, one, two, or three stethoscope probes are actuated while the other(s) is inactive.

The compliant extension may be constructed from a variety of mechanisms. These include, but are not limited to, an inflatable bladder, a spring, or a lever. In embodiments that include an inflatable bladder, air may be injected into the inflatable bladder causing it to expand toward the front section of the toilet seat. The one or more stethoscope probes on the outer surface of the inflatable bladder may then also be moved toward the front section of the toilet seat and, in the event that a user is seated on the medical toilet, toward the user's back.

After measurements are complete, air may be removed from the inflatable bladder causing it to contract. The one or more stethoscope probes may then move toward the rear section of the toilet seat and, in the event that a user is seated on the medical toilet, away from the user's back.

Embodiments of the compliant extension that include a spring may have one or more springs mounted on the toilet lid and the one or more stethoscope probes mounted on the ends of the springs nearest the front section of the toilet seat. The spring may extend out toward the front section of the toilet seat, thus moving the one or more stethoscope probes toward a seated user. After measurements are complete, the springs may then contract and move the one or more stethoscope probes back toward the rear section of the toilet seat and away from a seated user.

Embodiments that include a lever may include a means for moving the leaver up or down. A device within the medical toilet may apply force to a first end of the leaver which causes the lever to move around a pivot point. A second end of the lever may be connected to the stethoscope probe. The second end of the lever may move around a pivot point in response to the force applied to the first end of the lever. The second end of the lever may then apply force to the one or more stethoscope probes causing them to move toward the front section of the toilet seat or back towards the rear section of the toilet seat.

Some embodiments of the medical toilet may include a height adjustment apparatus. The height adjustment apparatus may move the one or more stethoscope probes up or down. The one or more stethoscope probes may be connected directly or indirectly to the height adjustment apparatus which may include a belt drive, a screw drive, an armature, a vertically mobile post, or a vertically mobile plate. By moving the one or more stethoscope probes up or down as the height adjustment apparatus moves, the medical toilet may collect measurements from different parts (upper or lower) of a user's back. The height adjustment apparatus may also be used to adjust for users of different heights.

In some embodiments, the height adjustment apparatus includes a belt which moves around two or more pulleys. The stethoscope probe(s) may be connected indirectly through the compliant extension to the outer surface of the belt. As the belt moves around the pulleys, the stethoscope probe(s) move up or down with the belt. The height of the stethoscope probe(s) is thereby adjusted.

The stethoscope probe(s) may also travel with the belt around the pulleys such that the stethoscope probe(s) faces away from the toilet seat. A sanitizing device, which may be an ultraviolet illuminator, may be positioned on the side of the belt and pulley system that is opposite the toilet seat. As the stethoscope probe(s) passes the ultraviolet illuminator, the ultraviolet light sanitizes the stethoscope probe(s). The stethoscope probe(s) then travel with the belt back around the belt and pulley system to face toward the toilet seat. The next user finds a sanitized stethoscope probe(s) upon approaching the medical toilet.

In some embodiments, the medical toilet may include a heating device. The heating device may heat the stethoscope probe(s) to provide the user with a more comfortable experience it takes measurements. The heating device may also heat the toilet seat. The user may choose to heat one or both of the stethoscope probe(s) and the toilet seat.

The medical toilet may include a sound recorder which may record the sounds detected by the stethoscope probe(s). The sound recorder may be connected to a controller which may conduct a variety of analyses of the recorded sounds. The controller may contain files that include information about the user. For example, the file may include the user's medical history, height, weight, gender, and recent measurements taken using laboratory test and other medical devices. The controller may compare the analysis of the sounds collected by the stethoscope probe(s) with information stored about the user. The controller may also compare the sounds collected by the stethoscope probe(s) with those of healthy individuals or individuals who have been diagnosed with certain illnesses. The controller may propose a possible diagnosis based on these comparisons. The diagnoses may include, but are not limited to, tachycardia, bradycardia, heart failure, defective heart valves, arrhythmia, asthma, and pneumonia.

The medical toilet may further include a data port which may be connected to the controller. The data port may be used to transmit the sounds collected by the stethoscope probe(s) and recorded by the sound recorder to machines that are external to the medical toilet. These external machines may be external networks including cloud networks and controllers to which a healthcare provider has access. The analysis of the sounds as well as the comparison to other information as discussed herein may also be transmitted through the data port.

The medical toilet may include one or more feedback mechanisms which indicate to a user that a measurement is in progress or has been completed. The signal may include, but is not limited to, a haptic signal, an audible signal, or a visual signal. For example, the user may be instructed to remain motionless while the stethoscope probe(s) collect sound measurements. The user may perceive the feedback signal as an indication that the user may move about without disrupting the measurement. The feedback mechanisms may also indicate that the user is not positioned properly or moving too much to collect a useful measurement. Thus, the feedback mechanisms may send a signal prior to collecting measurements through the stethoscopes.

The medical toilet may include one or more different types of stethoscopes. For example, the medical toilet may include one or more of an acoustic stethoscope, electronic stethoscope, and a noise reduction stethoscope. One or more of the different types of stethoscopes may be used at any given time.

Some embodiments of the medical toilet may include a cover over the toilet lid. The cover may move down to cover the toilet lid, including the stethoscope probe(s) when the medical toilet is not in use. In some embodiments, the cover may move down when the toilet lid is lowered and move up with the toilet lid is raised. The cover may prevent damage to the stethoscope probe(s) or soiling of the toilet lid and stethoscope probe(s) when not in use. In some embodiments, the cover may move up to expose the stethoscope probe(s) when a sensor detects the presence of a user. The sensor may be a motion sensor, a weight sensor which detects the user's weight on the toilet set or in front of the toilet, or other sensor known in the art.

In some embodiments, the medical toilet includes an ultraviolet illuminator inside the cover. The ultraviolet illuminator may emit ultraviolet light which may sanitized the toilet lid and the stethoscope probe(s) between uses.

Figure 1A:
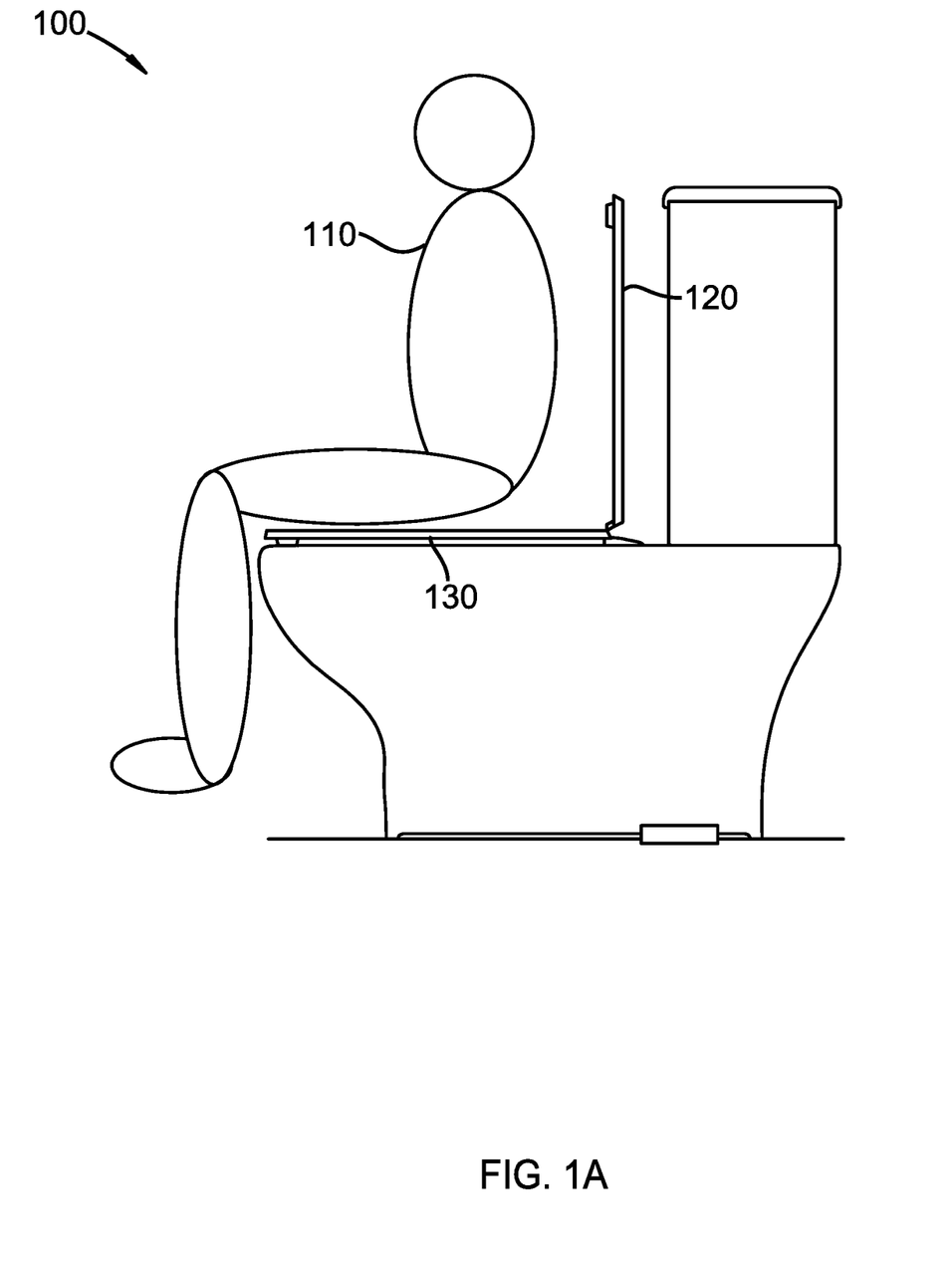
FIG. 1A is a schematic drawing of a user sitting on a toilet before the device has actuated according to the disclosure.

Referring now to the drawings, FIG. 1A illustrates toilet 100 which is an embodiment of the invention, with user 110 sitting on toilet seat 130. Toilet 100 includes toilet seat 120. At this point, the stethoscope within toilet 100 has not been actuated and toilet 100 resembles a traditional toilet.

Figure 1B:
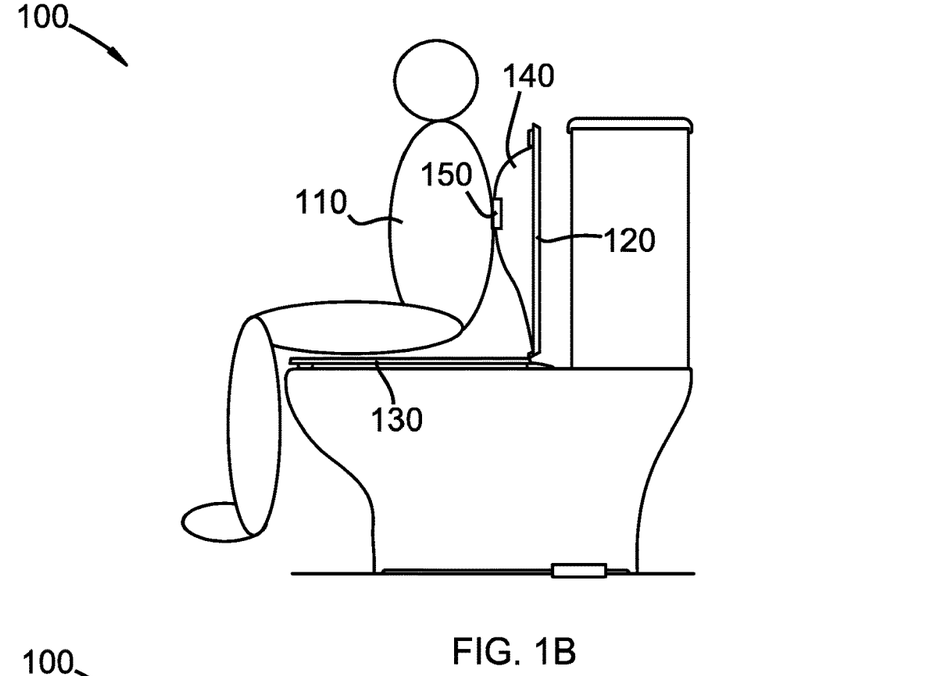
FIG. 1B is the user of FIG. 1A after the device has actuated to detect sound from the user's upper back.

FIG. 1B illustrates toilet 100, after the stethoscope has been actuated. This embodiment includes inflatable bladder 140 on which is shown stethoscope probe 150. Inflatable bladder 140 has expanded placing stethoscope probe 150 against the upper back of user 110.

Figure 1C:
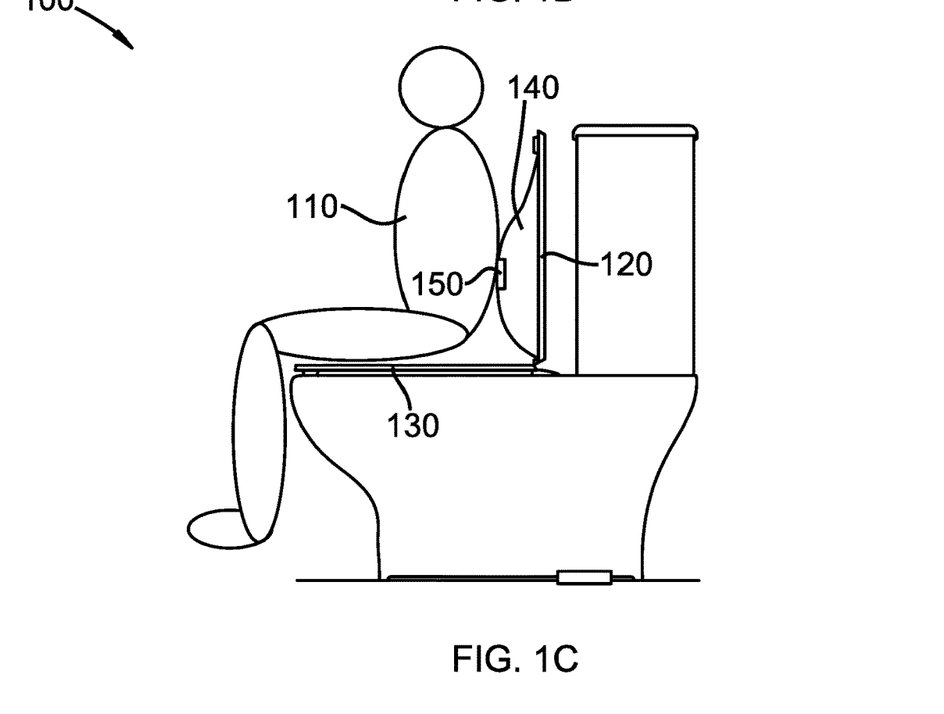
FIG. 1C is the user of FIG. 1A after the device has actuated to detect sound from the user's lower back.

FIG. 1C illustrates toilet 100, again after the stethoscope has been actuated. This drawing illustrates the variable height of stethoscope probe 150. Specifically, stethoscope probe 150 is shown lower on the back of user 110 than FIG. 1B. This feature allows the device to obtain measurements from users of different sizes and from different sites on the user's body.

Figure 2:
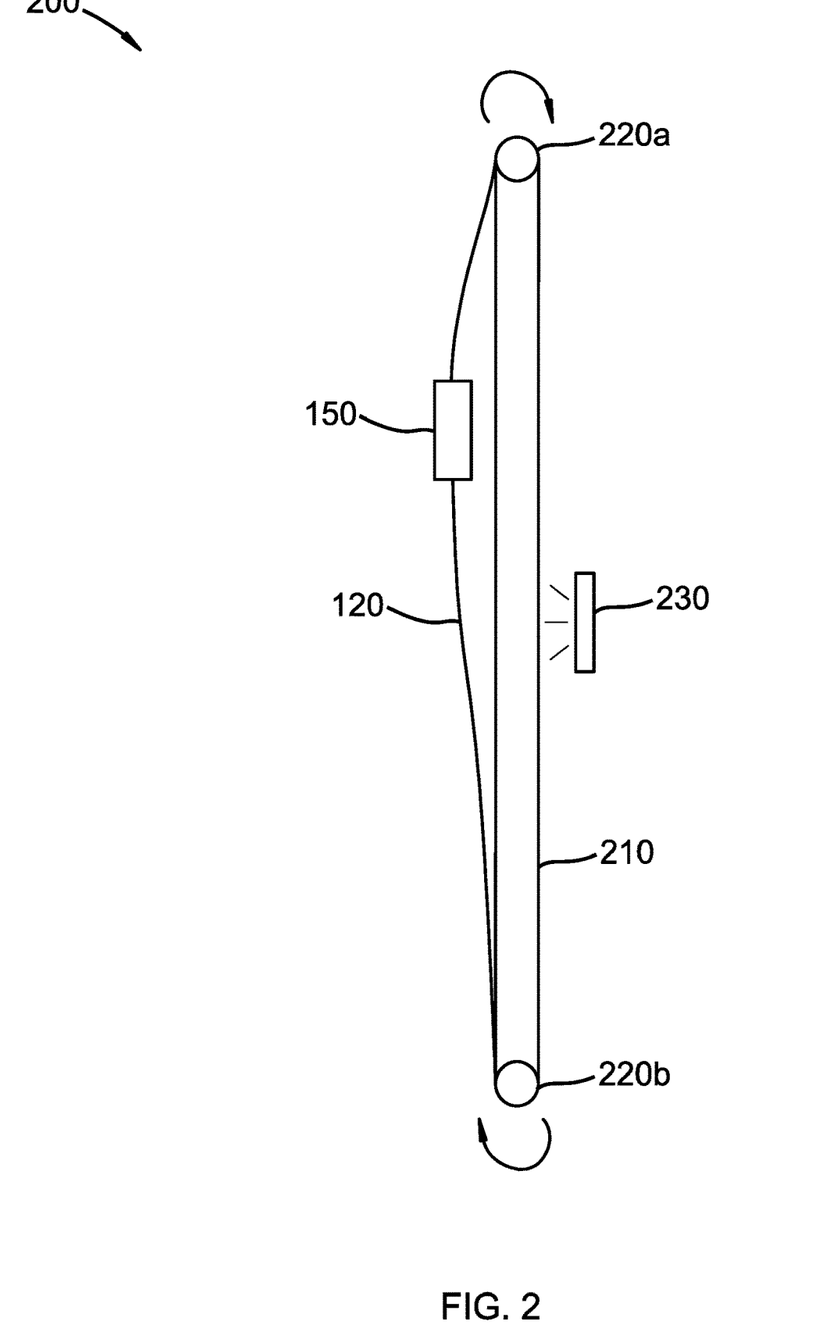
FIG. 2 is a schematic drawing of a stethoscope probe according to the disclosure moving around a belt to be disinfected.

FIG. 2 illustrates embodiment 200 of the disclosed device in which stethoscope probe 150 and inflatable bladder 120 are mounted on belt 210. Belt 210 winds around pulleys 220a and 220b. The arrows show the direction of movement of belt 210. As belt 210 moves around pulleys 220a and 220b, stethoscope probe 150 rises. This is one embodiment of a mechanism which may be used to adjust the height of the stethoscope probes. Stethoscope probe 150 may also travel to the other side of embodiment 200. As it does so, stethoscope probe 150 may travel past ultraviolet illuminator 230 which disinfects stethoscope probe 150. Belt 210 may then continue to move stethoscope probe 150 around pulley 210b. Stethoscope probe 150 may eventually reach its original position having been disinfected and ready for the next user.

Figure 3:
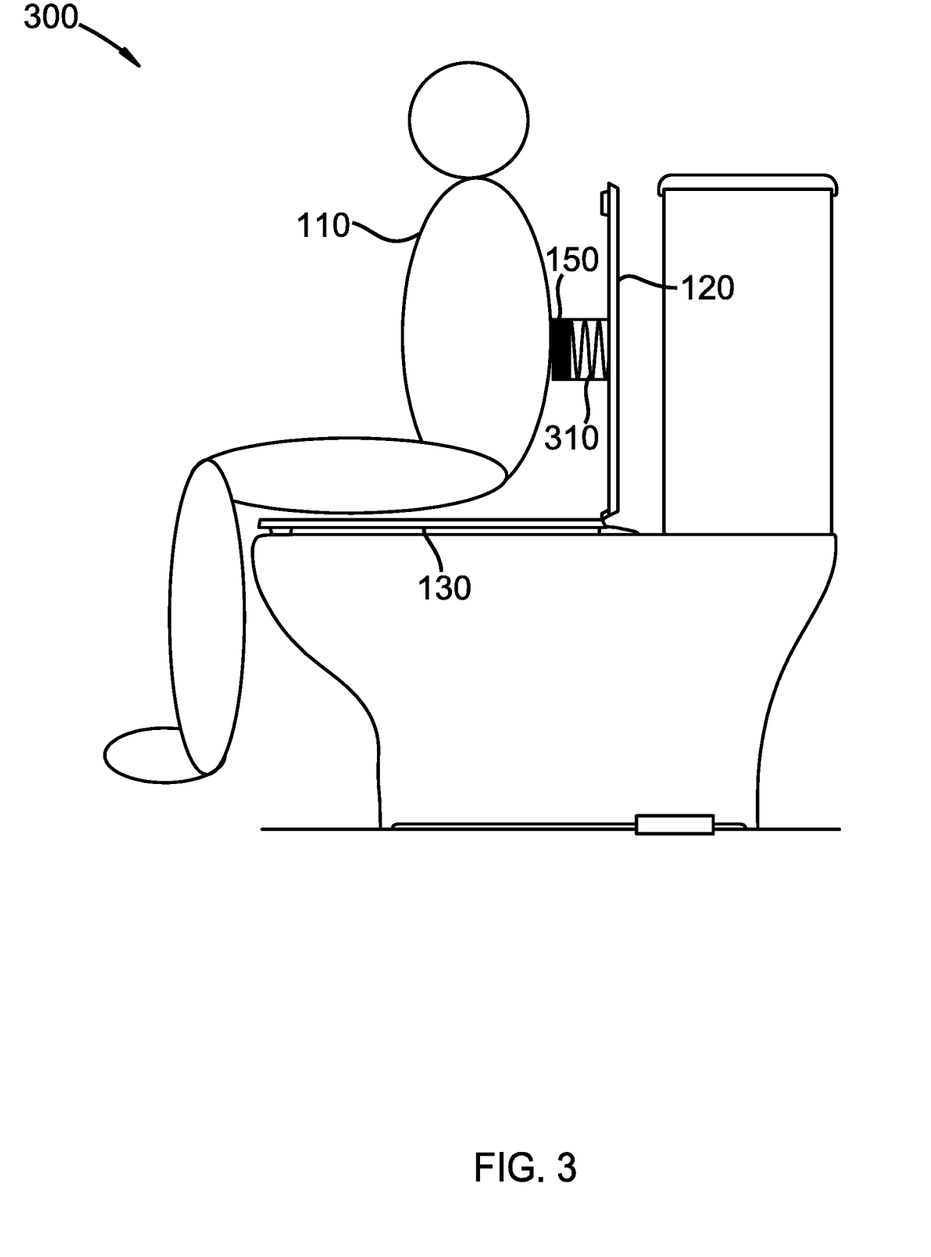
FIG. 3 is a schematic drawing of a user sitting on a toilet according to the disclosure with the stethoscope probe extended by a spring.

FIG. 3 illustrates toilet 300 which is another embodiment of the disclosed invention. In this embodiment, spring 310 is used to extend and retract stethoscope probe 150. Spring 310 performs approximately the same function as the inflatable bladder shown in other embodiments.

Figure 4:
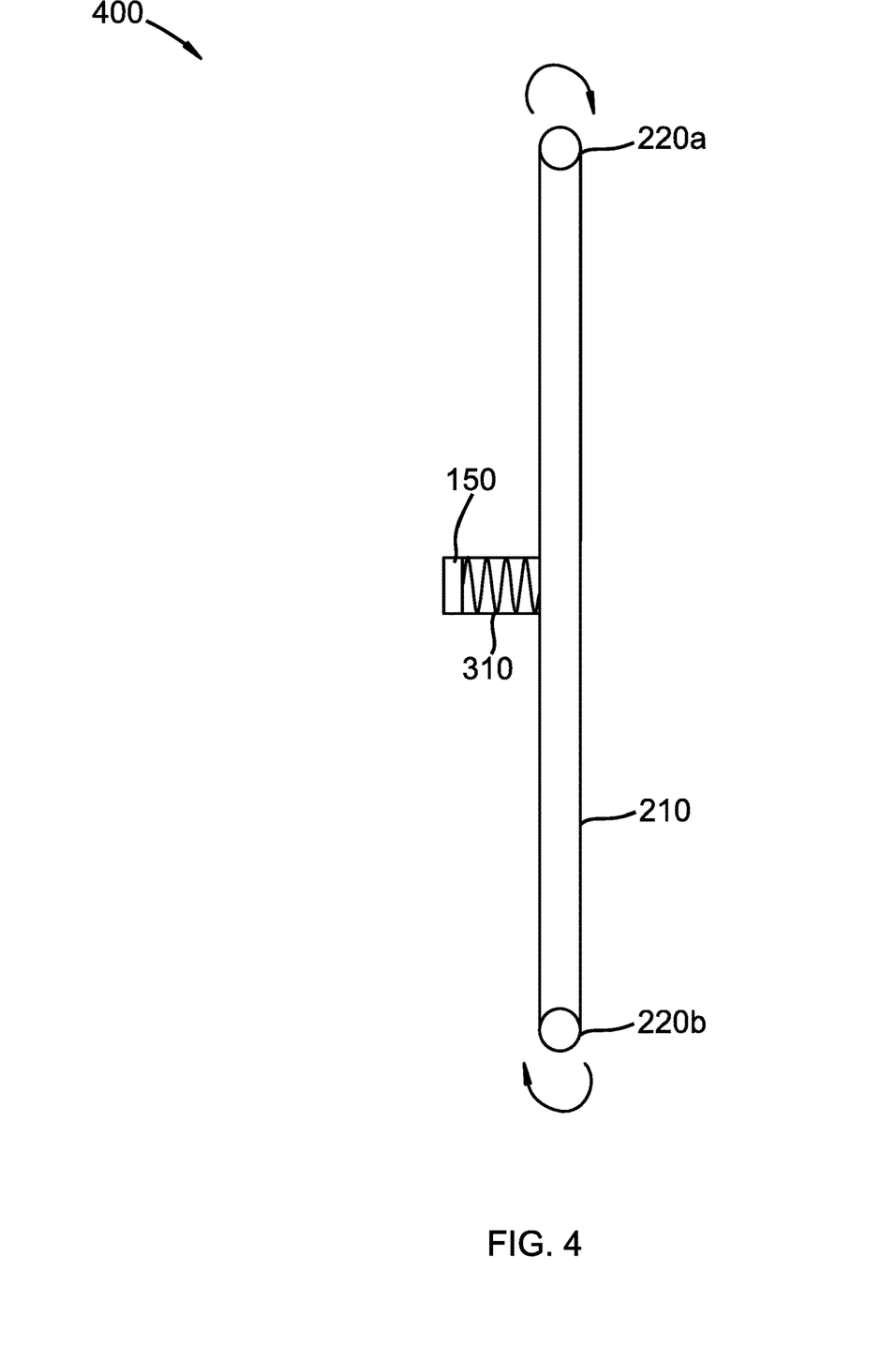
FIG. 4 is a schematic drawing of a stethoscope probe according to the disclosure adjusting its height by moving along a belt with the stethoscope probe extended by a spring.

FIG. 4 illustrates embodiment 400 which may be used to adjust the height of stethoscope probe 150. This embodiment includes spring 310 on belt 210. This embodiment is similar to FIG. 2 in which belt 210 moves inflatable bladder 120 and stethoscope probe 150. In embodiment 400, belt 210 moves around pulleys 220a and 220b causing spring 310 and stethoscope probe 150 to move with belt 210. The height of stethoscope probe 150 may be adjusted accordingly.

Figure 5:
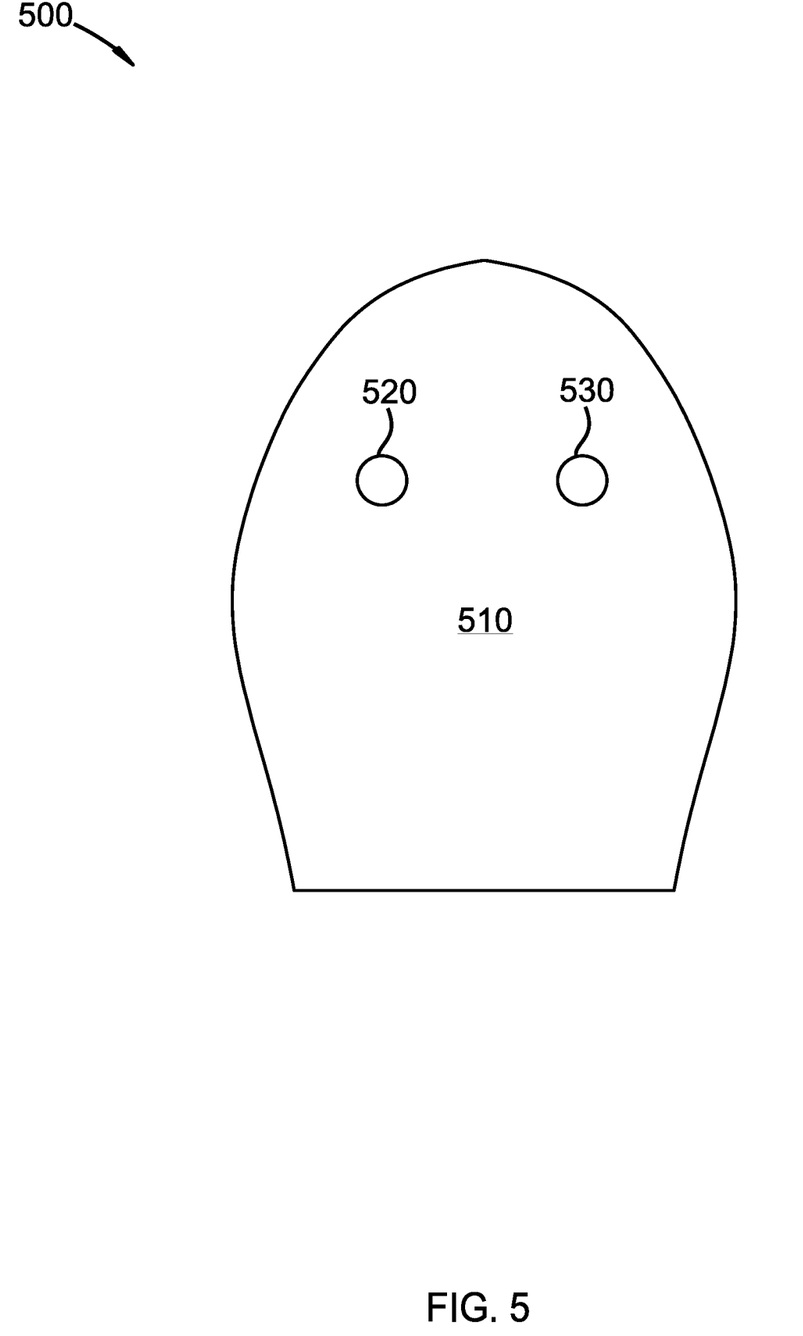
FIG. 5 is a schematic drawing of a toilet lid with two stethoscope probes according to the disclosure.

FIG. 5 illustrates toilet lid 500 which includes stethoscope probes 520 and 530. The presence of two stethoscope probes, each at a different position on toilet lid 500 enables the device to collect measurements from both the left and right side of a user. Additionally, the presence of two stethoscope probes enables the device to conduct two measurements at the same time. Alternatively, one of stethoscope probes 520 and 530 may be used at a time while the other is not actuated.

Figure 6:
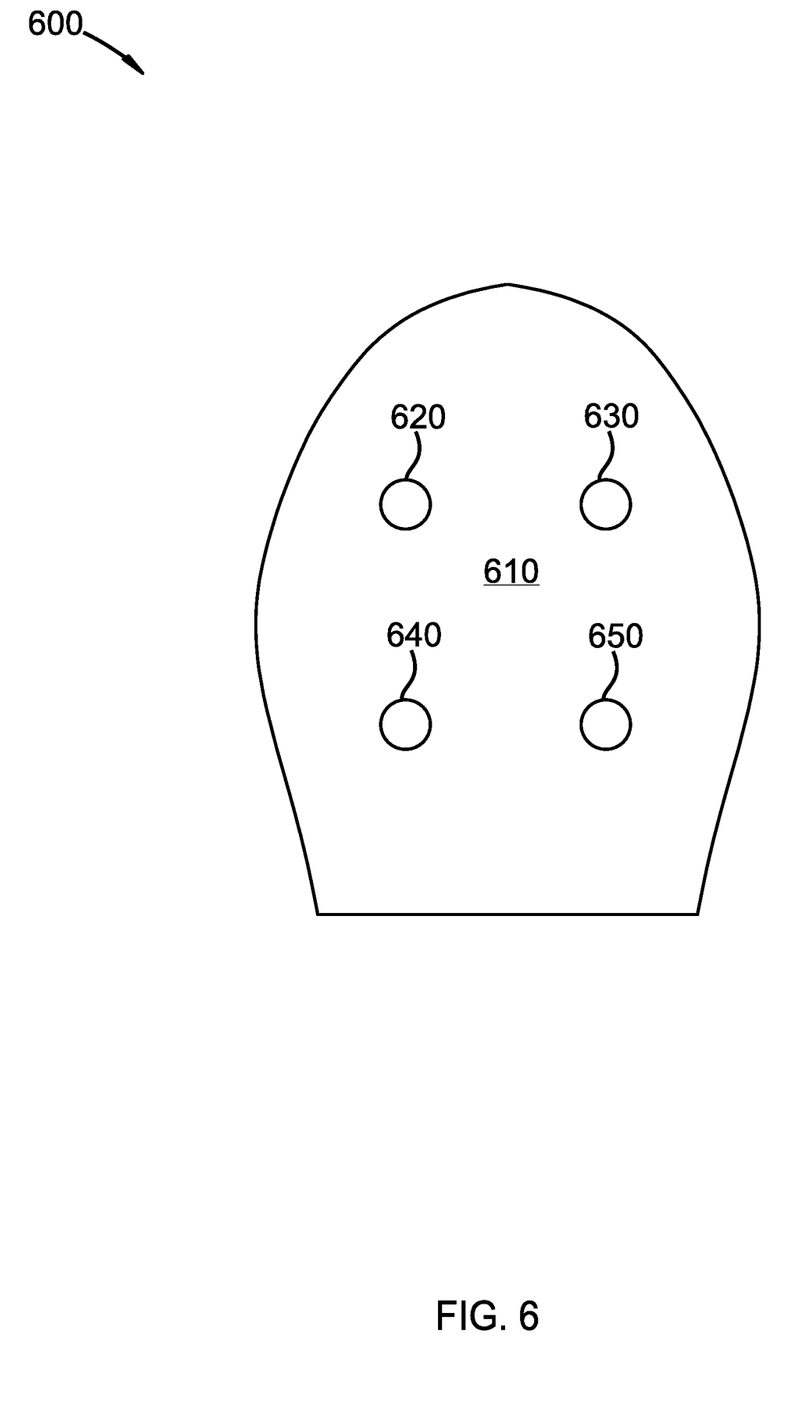
FIG. 6 is a schematic drawing of a toilet lid with four stethoscope probes according to the disclosure.

FIG. 6 illustrates toilet lid 600 which includes stethoscope probes 620, 630, 640, and 650. The advantages of the presence of four stethoscope probes is similar to those described with regard to two stethoscope probes. Specifically, measurements may be taken from four different positions on a user's body and four different measurements may be taken simultaneously. In addition, any combination of stethoscope probes 620, 630, 640, and 650 may be used at a given time while the remaining stethoscope probe is not actuated. Furthermore, each of the stethoscope probes in either FIG. 5 or FIG. 6 may be connected to a different type of stethoscope.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:
1. A medical toilet, the medical toilet comprising:
   a toilet, the toilet comprising:
      a toilet seat, the toilet seat comprising a front section and a rear section;
      a toilet lid, wherein the lid is positioned at the rear section of the toilet seat;
      a compliant extension, wherein the compliant extension reversibly is connected to the toilet lid, wherein the compliant extension extends from the toilet lid towards the front section of the toilet seat, and wherein the compliant extension comprises an outer surface;
      at least one stethoscope probe, wherein the at least one stethoscope probe is in connection with the outer surface of the compliant extension,
      at least one stethoscope, wherein the at least one stethoscope is in connection with the at least one stethoscope probe
      a belt; and
      at least two pulleys, wherein the belt moves around the at least two pulleys, wherein the at least one stethoscope probe is in connection with the belt, and wherein the belt moves around the at least two pulleys thereby moving the at least one stethoscope probe around the at least two pulleys.

2. The medical toilet of claim 1, further comprising an ultraviolet illuminator, wherein the stethoscope probe moves past the ultraviolet illuminator as the belt moves around the at least two pulleys.

3. A medical toilet, the medical toilet comprising:

a toilet, the toilet comprising:

- a toilet seat, the toilet seat comprising a front section and a rear section;
- a toilet lid, wherein the lid is positioned at the rear section of the toilet seat;
- a compliant extension, wherein the compliant extension reversibly is connected to the toilet lid, wherein the compliant extension extends from the toilet lid towards the front section of the toilet seat, and wherein the compliant extension comprises an outer surface;
- at least one stethoscope probe, wherein the at least one stethoscope probe is in connection with the outer surface of the compliant extension,
- at least one stethoscope, wherein the at least one stethoscope is in connection with the at least one stethoscope probe; and
- a cover, wherein the cover is in connection with the toilet lid, wherein the cover moves down to cover the at least one stethoscope probe as the toilet lid is lowered, and wherein the cover moves up to expose the at least one stethoscope probe when the toilet lid is raised.

4. The medical toilet of claim 3, wherein an ultraviolet illuminator is located on an inner side of the cover, and wherein the ultraviolet illuminator disinfects the at least one stethoscope probe when the cover is moves down to cover the at least one stethoscope probe.

* * * * *